US008951738B2

(12) United States Patent
Andres et al.

(10) Patent No.: US 8,951,738 B2
(45) Date of Patent: *Feb. 10, 2015

(54) CYBP AS A MARKER FOR LUNG CANCER

(75) Inventors: Herbert Andres, Penzberg (DE);
Johann Karl, Peissenberg (DE); Julia Riedlinger, Munich (DE); Markus Roessler, Germering (DE); Michael Tacke, Munich (DE); Michael Thierolf, Schlehdorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 256 days.

This patent is subject to a terminal disclaimer.

(21) Appl. No.: 13/270,482

(22) Filed: Oct. 11, 2011

(65) Prior Publication Data

US 2012/0196303 A1 Aug. 2, 2012

Related U.S. Application Data

(63) Continuation of application No. PCT/EP2010/056730, filed on May 17, 2010.

(30) Foreign Application Priority Data

May 15, 2009 (EP) .................................... 09006609

(51) Int. Cl.
*G01N 33/53* (2006.01)
*G01N 33/574* (2006.01)
(52) U.S. Cl.
CPC .. *G01N 33/57423* (2013.01); *G01N 2333/4727* (2013.01)
USPC .......................................... 435/7.1; 435/7.23
(58) Field of Classification Search
CPC ................................................ G01N 33/57423
See application file for complete search history.

(56) References Cited

U.S. PATENT DOCUMENTS

2006/0240441 A1* 10/2006 Taylor et al. ...................... 435/6
2012/0021929 A1* 1/2012 Swiatek-de Lange et al. ... 506/7

FOREIGN PATENT DOCUMENTS

| WO | 2005/032495 A3 | 4/2005 |
| WO | 2006/071081 A1 | 7/2006 |
| WO | 2007/076439 A3 | 7/2007 |
| WO | 2008/116592 A1 | 10/2008 |
| WO | 2009/006323 A3 | 1/2009 |

OTHER PUBLICATIONS

Stratagene Catalog (1988, p. 39).*
Herbert et al. (The Dictionary of Immunology, Academic Press, 4th edition, 1995, p. 58).*
Greenspan et al. (Nature Biotechnology 7:936-937 (1999).*
International Search Report issued Sep. 30, 2010 in PCT Application No. PCT/EP2010/056730.
International Preliminary Report on Patentability issued Aug. 1, 2011 in PCT Application No. PCT/EP2010/056730.
Breiman, Leo, "Random Forests," Machine Learning, 2001, pp. 5-32, vol. 45.
Buccheri, Gianfranco and Ferrigno, Domenico, "Identifying Patients at Risk of Early Postoperative Recurrence of Lung Cancer: A New Use of the Old CEA Test," The Annals of Thoracic Surgery, 2003, pp. 973-980, vol. 75.
Calabretta, Bruno et al., "Molecular Cloning of the cDNA for a Growth Factor-inducible Gene with Strong homology to S-100, a Calcium-binding Protein," The Journal of Biological Chemistry, Sep. 25, 1986, pp. 12628-12632, vol. 201, No. 27.
Calabretta, Bruno et al., "Altered expression of G1-specific genes in human malignant myeloid cells," Proceedings of the National Academy of Sciences, Mar. 1986, pp. 1495-1498, vol. 83.
Duffy, M. J., "Clinical Uses of Tumor Markers: A Critical Review," Critical Reviews in Clinical Laboratory Sciences, 2001, pp. 225-262, vol. 38, No. 3.
Filipek, Anna and Wojda, Urszula, "p30, a novel protein target of mouse calcyclin (S100A6)," Biochemistry Journal, 1996, pp. 585-587, vol. 320.
Filipek, Anna et al., "Characterization of the cell-cycle-regulated protein calcyclin from Ehrlich ascites tumor cells," European Journal of Biochemistry, 1991, pp. 795-800, vol. 195.
Filipek, Anna and Kuźnicki, Jacek, "Molecular Cloning and Expression of a Mouse Brain cDNA Encoding a Novel Protein Target of Calcyclin," Journal of Neurochemistry, 1998, pp. 1793-1798, vol. 70.
Friedman, Jerome H., "Regularized Discriminant Analysis," Journal of the American Statistical Association, Mar. 1989, pp. 165-175, vol. 84, No. 405.
Fukasawa, Toshio et al., "Clinical Evaluation of Serum NSE and CEA in Primary Lung Cancer Patients," Japanese Journal of Cancer and Chemotherapy, May 1986, pp. 1862-1867, vol. 13, No. 5, Abstract in English.
Guo, Xiaojia et al., "Identification of a Serum-inducible Messenger RNA (5B10) as the Mouse Homologue of Calcyclin: Tissue Distribution and Expression in Metastatic, ras-transformed NIH 3T3 Cells," Cell Growth & Differentiation, Jul. 1990, pp. 333-338, vol. 1.
Heizmann, Claus W. and Cox, Jos A., "New perspectives on S100 proteins: a multi-function Ca2+-, Zn2+- and Cu2 +-binding protein family," BioMetals, 1998, pp. 383-397, vol. 11.
Jastrzebska, Beata et al., "Calcyclin (S100A6) Binding Protein (CacyBP) Is Highly Expressed in Brain Neurons," The Journal of Histochemistry & Cytochemistry, 2000, pp. 1195-1202, vol. 48, No. 9.
Kuźnicki, J. et al., "Calcyclin as a Marker of Human Epithelial Cells and Fibroblasts," Experimental Cell Research, 1992, pp. 425-430, vol. 200.
Kuźnicki, Jacek et al., "Calcium-binding protein from mouse Ehrlich ascites-tumour cells is homologous to human calcyclin," Biochemistry Journal, 1989, pp. 951-956, vol. 263.

(Continued)

*Primary Examiner* — Peter J Reddig
(74) *Attorney, Agent, or Firm* — Denise M. Everett

(57) ABSTRACT

The present invention relates to the assessment of lung cancer. It discloses the use of protein CYBP in the assessment of lung cancer. It also relates to a method for assessing lung cancer in vitro using a liquid sample, derived from an individual by measuring CYBP in said sample. Measurement of CYBP can, e.g., be used in the early detection or in the follow-up of patients with lung cancer.

14 Claims, No Drawings

(56) References Cited

OTHER PUBLICATIONS

Kuźnicki, Jacek and Filipek, Anna, "Purification and properties of a novel Ca2+-binding protein (10.5 kDa) from Ehrlich-ascites-tumour cells," Biochemistry Journal, 1987, pp. 663-667, vol. 247.

Leonard, Debra G. B. et al., "Identification and Characterization of mRNAs Regulated by Nerve Growth Factor in PC12 Cells," Molecular and Cellular Biology, Sep. 1987, pp. 3156-3167, vol. 7, No. 9.

Mani, Rajam S. and Kay, Cyril M., "Calcium-Dependent Regulation of the Caldesmon-Heavy Meromyosin Interaction by Caltropin," Biochemistry, 1993, pp. 11217-11223, vol. 32.

Merle, P. et al., "Early CYFRA 21-1 variation predicts tumor response to chemotherapy and survival in locally advanced non-small cell lung cancer patients," The International Journal of Biological Markers, pp. 310-315, vol. 19, No. 4.

Molina, R. et al., "Tumor Markers (CEA, CA 125, CYFRA 21-1, SCC and NSE) in Patients with Non-Small Cell Lung Cancer as an Aid in Histological Diagnosis and Prognosis Comparison with the Main Clinical and Pathological Prognostic Factors," Tumor Biology, 2003, pp. 209-218, vol. 24.

Potts, Barbara C. M. et al., "The structure of calcyclin reveals a novel homodimeric fold for S100 Ca2+-binding proteins," Nature Structural Biology, Sep. 1995, pp. 790-796, vol. 2, No. 9.

Ruczinski, Ingo et al., "Logic Regression," Journal of Computational and Graphical Statistics, 2003, pp. 475-511, vol. 12, No. 3.

Schneider, Joachim et al., "Fuzzy logic-based tumor-marker profiles improved sensitivity in the diagnosis of lung cancer," International Journal of Clinical Oncology, 2002, pp. 145-151, vol. 7.

Schneider, Joachim, "Tumor Markers in Detection of Lung Cancer," Advances in Clinical Chemistry, Jan. 2006, pp. 1-41, vol. 42.

Tokumitsu, Hiroshi et al., "Molecular Cloning of Rabbit CAP-50, a Calcyclin-Associated Annexin protein," Biochemical and Biophysical Research Communications, Aug. 14, 1992, pp. 1227-1235, vol. 186, No. 3.

Tonini, Gian Paolo et al., "Inducible Expression of Calcyclin, a Gene with Strong Homology to S-100 Protein, during Neuroblastoma Cell Differentiation and Its Prevalent Expression in Schwann-like Cell Lines," Cancer Research, Mar. 15, 1991, pp. 1733-1737, vol. 51.

Wagner, Henry Jr., "Postoperative Adjuvant Therapy for Patients With Resected Non-Small Cell Lung Cancer: Still Controversial After all These Years," Chest, 2000, pp. 110S-118S, vol. 117.

Zeng, Fu-Yue et al., "Identification of Annexin II, Annexin VI and Glyceraldehyde-3-Phosphate Dehydrogenase as Calcyclin-Binding Proteins in Bovine Heart," International Journal of Biochemistry, 1993, pp. 1019-1027, vol. 25, No. 7.

Zhai, Huihong et al., "Expression of Calcyclin-binding Protein/Siah-1 Interacting Protein in Normal and Malignant Human Tissues: An Immunohistochemical Survey," Journal of Histochemistry & Cytochemistry, 2008, pp. 765-772, vol. 56, No. 8.

Zimmer, Danna B. et al., "The S100 Protein Family: History, Function, and Expression," Brain Research Bulletin, 1995, pp. 417-429, vol. 37, No. 4.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

\* cited by examiner

CYBP AS A MARKER FOR LUNG CANCER

RELATED APPLICATIONS

This application is a continuation of PCT/EP2010/056730 filed May 17, 2010 and claims priority to EP 09006609.3 filed May 15, 2009.

SEQUENCE LISTING

The instant application contains a Sequence Listing which has been submitted in ASCII format via EFS-Web and is hereby incorporated by reference in its entirety. Said ASCII copy, created on Oct. 10, 2011, is named 25394US.txt, and is 4,883 bytes in size.

FIELD

The present invention relates to a method aiding in the assessment of pulmonary or lung cancer (LC) and in particular in the assessment of non-small cell lung carcinoma (NSCLC). It discloses the use of the "calcyclin-binding protein" (CYBP) as a marker of LC, particularly of NSCLC. Furthermore, it especially relates to a method for assessing lung cancer from a liquid sample, derived from an individual by measuring CYBP in said sample. Measurement of CYBP can, e.g., be used in the early detection of lung cancer or in the surveillance of patients who undergo surgery.

BACKGROUND

Cancer remains a major public health challenge despite progress in detection and therapy. Amongst the various types of cancer, LC is a frequent cancer in the Western world and among the most frequent causes of cancer-related mortality. This is in large part due to the diagnostic gap for early detection of the disease. LC is largely asymptomatic in its early stages. The majority of all lung cancers is detected at a late stage when the disease has already become inoperable.

The majority of LC tumors can be divided into small cell lung carcinoma (SCLC) and non-small cell lung carcinoma (NSCLC). SCLC accounts for about 20-25% of all lung cancer cases. SCLC is an aggressive neuroendocrine type of LC and has a very poor prognosis even if detected in early stages. SCLC is rarely amenable to curative treatment by resection. Because of the speed with which the disease progresses, SCLC is generally categorized using only two stages, i.e., limited and extensive disease, rather than the more complex TNM staging system (see below). About 75-80% of LC cases are grouped into the class of NSCLC including squamous cell carcinoma (carcinoma=CA), adeno CA (comprising the subclasses of acinar CA, papillary CA, bronchoalveolar tumor, solid tumor, and mixed subtypes), and large cell carcinoma (comprising the subclasses of giant cell tumors, clear cell CA, adenosquamous CA, and undifferentiated CA).

NSCLC, if detected at late stages, also has a very poor prognosis. The staging of cancer is the classification of the disease in terms of extent, progression, cell type and tumor grade. It groups cancer patients so that generalizations can be made about prognosis and the choice of therapy.

Today, the TNM system is the most widely used classification system based on the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), edition, 1997 (Sobin, L. H., and Fleming, I. D., TNM 80 (1997) 1803-4).

Surgical resection of the primary tumor is widely accepted as the treatment of choice for early stage NSCLC. With the progression of NSCLC and, more specifically, the transition from stage Ma (T3N1M0, T1N2M0, T2N2M0, T3N2M0) to Mb (T4N0M0, T4N1M0, T4N2M0), a significant shift in the physician's approach is precipitated. However, if the cancer is detected during the more early stages (Ia-IIIa; preferably up to stage T3N1M0), the five-year survival rate varies between 35% and 80%. Detection at stage Ia ((T1N0M0); small tumor size, no metastasis) has evidently the best prognosis with a five-year survival of up to 80%.

Surgery is rarely, if ever, used in the management of stage IIIb-IV of NSCLC. Stage IV corresponds to distant metastasis, i.e., spread of the disease beyond the lungs and regional lymph nodes. The five-year survival rate in the later stages III and IV drops to between less than 15% and 1%, respectively.

What is especially important is, that early diagnosis of NSCLC translates to a much better prognosis. Patients diagnosed as early as in stage Ia (T1N0M0), Ib (T2N0M0), IIa (T1N1M0), IIb, (T3N0M0), and IIIa (T3N1M0), if treated properly have an up to 80% chance of survival 5 years after diagnosis. This has to be compared to a 5-years survival rate of less than 1% for patients diagnosed once distant metastases are already present.

In the sense of the present invention early assessment of LC refers to an assessment at a tumor stage of between Ia and Ma, as defined above.

It is preferred that LC is assessed at a stage of between Ia and IIIa.

Most lung cancers are detected when they become symptomatic. Current detection methods include chest x-ray, spiral computer tomography, sputum cytology and bronchioscopy. However, there is controversy regarding the suitability of these means for mass screenings.

A number of serum tumor markers for lung cancers are in clinical use. The soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose (2000) TH Books Verlagsgesellschaft, Frankfurt/Main, Germany).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum and plasma are the most widely used sources of sample in clinical routine. The identification of an early LC tumor marker that would aid in the reliable cancer detection or provide early prognostic information could lead to a method that would greatly aid in the diagnosis and in the management of this disease. Therefore, an urgent clinical need exists to improve the in vitro assessment of LC. It is especially important to improve the early diagnosis of LC, since for patients diagnosed early on chances of survival are much higher as compared to those diagnosed at a progressed stage of disease. Especially, there is an urgent need for methods for reliable monitoring of a LC treatment, screening individuals for LC and testing for recurrence of lung cancer after LC therapy.

The clinical utility of biochemical markers in lung cancer has recently been reviewed (Duffy, M. J., Critical Reviews in Clinical Laboratory Sciences 38 (2001) 225-262).

CYFRA 21-1 is currently regarded to be the best of the presently known tumor markers for lung cancer. Even though not organ-specific, it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While the sensitivity for SCLC at 95% specificity is reported to be 60-87%, the performance of NSE testing for NSCLC is poor (sensitivity of 7-25%). NSE is recommended for therapy surveillance of SCLC.

ProGRP is a tumor marker, useful in the detection and monitoring of SCLC. Increased serum levels are also found in patients with nonmalignant lung/pleural diseases, such as idiopathic pulmonary fibrosis or sarcoidosis. While sensitivity for proGRP in the field of SCLC (at 95% specificity) is reported to be 47-86%, the performance of proGRP testing in the field of NSCLC is poor because the sensitivity is reported as being below 10%.

SCC was originally identified in squamous cell CA of the cervix. The sensitivity of SCC for LC in general is low (18-27%). Therefore, SCC testing is regarded to be not suitable for screening. However, due to a higher sensitivity for squamous cell CA, a preferred use for SCC is therapy surveillance, even though CYFRA 21-1 generally performs better.

In an immunohistochemical survey, Zhai et al. (Journal of Histochemistry and Cytochemistry, vol. 56(8): 765-772, 2008) have analysed the CacyBP protein expression profile in a broad range of human normal tissues and carcinomas by immunohistochemistry staining with a monoclonal anti-CacyBP antibody. In this study, CacyBP staining was observed in a variety of adenocarcinomas and squamous carcinomas. The percentage of positive staining was highest in nasopharyngeal carcinomas (71%), pancreas adenocarcinomas (70%), breast carcinomas (63%), and osteogenic sarcomas (63%). By comparison, only about 45% of lung adenocarcinoma samples and 50% of lung squamous carcinoma samples were stained.

With respect to marker profiles and aiming at improved diagnosis of lung cancer, a method was published (Schneider, J. et al. Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%. However, in this study, for example the sensitivity of CYFRA 21-1 as a single tumor marker is reported to be at 72% at a specificity of 95%, which is significantly higher than in many other reported studies. Duffy, M. J., in Critical Reviews in Clinical Laboratory Sciences 38 (2001) 225-262 report a sensitivity of between 46% and 61%. This unusual high performance achieved by Schneider et al., raises some doubts and might be due to several facts. Firstly, the collective of control patients seems to be younger than the patients collective, i.e. the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, it has to be expected that the same algorithm applied to a larger, independent, and well balanced validation set will lead to a significantly reduced overall performance.

It was the task of the present invention to investigate whether a biochemical marker can be identified which may be used in assessing LC.

Surprisingly, it has been found that use of the marker CYBP (Calcyclin-binding protein, CacyBP, Siah-interacting protein, S100A6-binding protein), particularly human CYBP (hCYBP), can at least partially overcome some of the problems of the markers presently known in the state of the art.

SUMMARY

The present invention relates to a method for assessing lung cancer in vitro comprising measuring in a sample the presence and/or concentration of CYBP, and using the measurement result, particularly the concentration determined in the assessment of lung cancer.

In preferred embodiments, the novel marker CYBP may be used for monitoring as well as for screening purposes.

When used in patient monitoring the diagnostic method according to the present invention may help to assess tumor load, efficacy of treatment and tumor recurrence in the follow-up of patients. Increased levels of CYBP are directly correlated to tumor burden. After chemotherapy a short term (few hours to 14 days) increase in CYBP may serve as an indicator of tumor cell death. In the follow-up of patients (from 3 months to 10 years) an increase of CYBP can be used as an indicator for tumor recurrence.

In a preferred embodiment the diagnostic method according to the present invention is used for screening purposes. I.e., it is used to assess subjects without a prior diagnosis of LC by measuring the level of CYBP and correlating the level measured to the presence or absence of LC.

The present invention is also directed to a method for assessing LC in vitro by biochemical markers, comprising measuring in a sample the presence and/or concentration of CYBP and of one or more other marker of LC and using the measurement results, particularly concentrations determined in the assessment of LC. It is preferred that the one or more other marker of LC is selected from the group consisting of CYFRA 21-1, CEA, NSE, proGRP and SCC.

The present invention also relates to the use of a marker panel comprising CYBP and one or more additional marker in the assessment of LC, wherein a preferred additional marker is selected from the group consisting of CYFRA 21-1, CEA, NSE, proGRP and SCC.

The present invention, in a preferred embodiment, also relates to the use of a marker panel comprising at least CYBP and CYFRA 21-1 in the assessment of LC.

The present invention also relates to the use of a marker panel comprising at least CYBP and CEA in the assessment of LC.

The present invention also relates to the use of a marker panel comprising at least CYBP and SCC in the assessment of LC.

The present invention further relates to a kit for performing the method according to the present invention comprising at least the reagents required to specifically measure CYBP and optionally auxiliary reagents for performing the measurement.

The present invention also provides a kit for performing the method according to the present invention comprising at least the reagents required to specifically measure CYBP and CYFRA 21-1, respectively, and optionally auxiliary reagents for performing the measurement.

The present invention also provides a kit for performing the methods according to the present invention comprising at least the reagents required to specifically measure CYBP and one or more other marker for lung cancer.

The present invention also provides a kit for performing the method according to the present invention comprising at least the reagents required to specifically measure CYBP and CEA, respectively, and optionally auxiliary reagents for performing the measurement.

The present invention also provides a kit for performing the method according to the present invention comprising at least the reagents required to specifically measure CYBP and SCC, respectively, and optionally auxiliary reagents for performing the measurement.

In a preferred embodiment the present invention relates to a method for assessing lung cancer in vitro comprising measuring in a sample the presence and/or concentration of a) CYBP, and b) optionally one or more other marker of lung cancer, and c) using the measurement results, particularly the concentrations determined in step (a) and optionally step (b) in the assessment of lung cancer.

DETAILED DESCRIPTION

The term "measurement" comprises a qualitative or a quantitative measurement of CYBP in a sample. In a preferred embodiment the measurement is a qualitative or semi-quantitative measurement, i.e., it is determined whether CYBP is present or absent or it is determined whether the concentration of CYBP is above or below a cut-off value. As the skilled artisan will appreciate, in a Yes-(presence) or No-(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. Presence of a value above the cut-off value can for example be indicative for the presence of lung cancer. In a further preferred embodiment the measurement is a quantitative measurement. In this embodiment the concentration of CYBP is correlated to an underlying diagnostic question like, e.g., stage of disease, disease progression, or response to therapy.

Calcyclin (S100A6) is a calcium-binding protein that belongs to the family of S100 proteins (reviewed in Zimmer et al., Brain Res. Bull. 37 (1995), 417-429; Heizmann and Cox, Biometals 11 (1998), 383-397). Its gene was discovered on the basis of its cell cycle-dependent expression (Calabretta et al., J. Biol. Chem. 261 (1986), 12628-12632). This gene is expressed at its maximal level during the transition between G0 to S phase of the cell cycle, but its expression is deregulated in acute myeloid leukemia (Calabretta et al., Proc. Natl. Sci USA 83 (1986), 1495-1498). The protein was first purified and characterized from Ehrlich ascites tumor (EAT) cells (Kuznicki and Filipek, Biochem. J. 247 (1987), 663-667; Kuznicki et al., Biochem. J. 263 (1989), 951-956). Later calcyclin was found to be expressed at high levels in fibroblasts and epithelial cells, in cells with high proliferating activity, and those undergoing differentiation (Leonard et al., Mol. Cell. Biol. 7 (1987), 3156-3167; Guo et al., Cell Growth Differ. 1 (1990), 333-338; Tonini et al., Cancer Res. Si (1991), 1733-1737, Kuznicki et al., Exp. Cell. Res. 200 (1992), 425-430).

Several possible protein targets of calcyclin have been identified. Calcyclin has been shown to interact in vitro in a $Ca^{2+}$-dependent manner with glyceraldehyde-3-phosphate dehydrogenase, annexin II (Filipek et al., Eur. J. Biochem. 195 (1991), 795-800), annexin VI (Zeng et al., Int. J. Biochem. 25 (1993), 1019-1027), annexin XI (Tokumitsu et al., Biochem. Biophys. Res. Comm. 186 (1992), 1227-1235) caldesmon (Mani et al., Biochemistry 2 (1993), 11217-11223), and CacyBP (calcyclin-binding protein) (Filipek and Kuznicki, J. Neurochem. 70 (1998), 1793-1798; Filipek and Wojda, Biochem. J. 320 (1996), 585-587). Although the three-dimensional structures of calcyclin in the absence and presence of calcium have been determined (Potts et al., Nat. Struct. Biol. 2 (1995), 790-796), the structural basis for target interactions and its putative role as a calcium sensor in the cell remain unclear.

CacyBP was initially identified, purified, and characterized from EAT cells (Filipek and Wojda (1996), supra). Amino acid sequencing of chymotryptic fragments suggested that it was a novel protein, so CacyBP was cloned from a mouse brain cDNA library and sequenced (Filipek and Kuznicki (1998), supra). The amino acid sequence of human CYBP (Swiss PROT Q9HB71) is depicted as SEQ ID NO: 1. Except for a recently submitted hypothetical protein, which is apparently a human homologue of CacyBP, the nucleotide sequence of CacyBP reveals no homology to any other sequence deposited in standard data bases. Recombinant CacyBP was expressed in *Escherichia coli*, and its interaction with calcyclin was shown to occur at physiological calcium concentration (Filipek and Kuznicki (1998), supra). Recent studies revealed that CacyBP is present at high level in the mouse and rat brain, particularly in the neuronal cells (Jastrzebska et al., J. Histochem. Cytochem. 48 (2000), 1195-1202).

CYBP may be involved in calcium-dependent ubiquitination and subsequent proteosomal degradation of target proteins. It probably serves as a molecular bridge in ubiquitin E3 complexes. It participates in the ubiquitin-mediated degradation of beta-catenin (CTNNB1).

CYBP interacts with proteins of the 5100 family S100A1, S100A6, S100B, S100P and S100A12 at physiological calcium concentrations. It is a component of some large E3 complex at least composed of UBE2D1, SIAH1, CACYBP/SIP, SKP1, APC and TBL1X. It interacts directly with SIAH1, SIAH2 and SKP1.

CYBP is localized in the nucleus and in cytoplasm at low calcium concentrations. In neuroblastoma cells, after a retinoic acid (RA) induction and calcium increase, it localizes in both the nucleus and cytoplasm. The nuclear fraction may be phosphorylated.

There is no suggestion in the art that a sensitive and specific determination of CYBP in tissue extracts and in body fluids would allow assessment of lung cancer. Surprisingly, it was found in the present invention that a determination of the presence and/or amount of CYBP in a tissue lysate sample and/or body fluid allows the assessment of lung cancer. CYBP can be measured with high sensitivity in body fluids such as blood, serum or plasma. Further, the inventors found out that a reliable assessment of LC is possible by measuring CYBP within a liquid sample from an individual, i.e., no tissue and no biopsy sample is required in diagnosis of LC when using protein CYBP as marker. Even more surprisingly it was found that an increased level of CYBP as measured from bodily fluid of an individual is associated with lung cancer.

As obvious to the skilled artisan, the present invention shall not be construed to be limited to the full-length protein CYBP of SEQ ID NO: 1. Physiological or artificial fragments of CYBP, secondary modifications of CYBP, as well as allelic variants of CYBP are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO: 1. Such fragment may advantageously be used for generation of antibodies or as a standard in an immunoassay. More preferred the artificial fragment comprises at least two epitopes of interest appropriate for setting up a sandwich immunoassay.

As used herein, each of the following terms has the meaning associated with it in this section.

The articles "a" and "an" are used herein to refer to one or to more than one (i.e., to at least one) of the grammatical object of the article. By way of example, "a marker" means one marker or more than one marker. The term "at least" is used to indicate that optionally one or more further objects may be present. By way of example, a marker panel comprising at least (the markers) CYBP and CYFRA 21-1 may optionally comprise one or more other marker.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. In one embodiment examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (PI) or molecular weight (MW), or both, e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Preferred posttranslational modifications are glycosylation, acylation, and/or phosphorylation.

Preferably the marker CYBP is specifically measured from a sample by use of a specific binding agent.

A specific binding agent is, e.g., a receptor for CYBP, a lectin binding to CYBP or an antibody to CYBP. A specific binding agent has at least an affinity of $10^7$ l/mol for its corresponding target molecule. The specific binding agent preferably has an affinity of $10^8$ l/mol or also preferred of $10^9$ l/mol for its target molecule. As the skilled artisan will appreciate the term specific is used to indicate that other biomolecules present in the sample do not significantly bind to the binding agent specific for CYBP. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity.

A specific binding agent preferably is an antibody reactive with CYBP. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108-115).

For the achievements as disclosed in the present invention polyclonal antibodies raised in rabbits may be used. However, clearly also polyclonal antibodies from different species, e.g., rats or guinea pigs, as well as monoclonal antibodies can be used. Since monoclonal antibodies can be produced in any amount required with constant properties, they represent ideal tools in development of an assay for clinical routine. The generation and the use of monoclonal antibodies to CYBP in a method according to the present invention, respectively, represent yet other preferred embodiments.

As the skilled artisan will appreciate now that CYBP has been identified as a marker which is useful in the assessment of lung cancer, various immunodiagnostic procedures may be used to reach a result comparable to the achievements of the present invention. For example, alternative strategies to generate antibodies may be used. Such strategies comprise amongst others the use of synthetic peptides, representing an epitope of CYBP for immunization. Alternatively, DNA immunization also known as DNA vaccination may be used.

For measurement the sample obtained from an individual is incubated with the specific binding agent for CYBP under conditions appropriate for formation of a binding agent CYBP-complex. Such conditions need not be specified, since the skilled artisan without any inventive effort can easily identify such appropriate incubation conditions. The amount of binding agent CYBP-complex is measured and used in the assessment of lung cancer. As the skilled artisan will appreciate there are numerous methods to measure the amount of the specific binding agent CYBP-complex all described in detail in relevant textbooks (cf., e.g., Tijssen P., supra, or Diamandis, E. P. and Christopoulos, T. K. (eds.), Immunoassay, Academic Press, Boston (1996)).

Preferably CYBP is detected in a sandwich type assay format. In such assay a first specific binding agent is used to capture CYBP on the one side and a second specific binding agent, which is labeled to be directly or indirectly detectable, is used on the other side.

In a preferred embodiment, measurement of CYBP in a sample is carried out by using a sandwich immunoassay, wherein Streptavidin-coated microtiter plates are used. A biotinylated polyclonal antibody to CYBP is used as a capturing antibody and a digoxigenylated polyclonal antibody to CYBP is used as the second specific binding partner in this sandwich assay. The sandwich complex formed is finally visualized by an anti-digoxigenin horseradish peroxidase conjugate and an appropriate peroxidase substrate.

As mentioned above, CYBP can be measured from a liquid sample obtained from an individual sample. No tissue and no biopsy sample is required to apply the marker CYBP in the diagnosis of LC.

In a preferred embodiment the method according to the present invention is practiced with plasma as liquid sample material.

A "marker of lung cancer" in the sense of the present invention is any marker that, if combined with the marker CYBP, adds relevant information in the assessment of LC. The information is considered relevant or of additive value if at a given specificity the sensitivity, or if at a given sensitivity the specificity, respectively, for the assessment of LC can be improved by including said marker into a marker combination already comprising the marker CYBP. Preferably the improvement in sensitivity or specificity, respectively, is statistically significant at a level of significance of p=0.05, 0.02, 0.01 or lower. Preferably, the one or more other marker of LC is selected from the group consisting of CYFRA 21-1, CEA, NSE, proGRP and SCC.

The term "sample" as used herein refers to a biological sample obtained for the purpose of evaluation in vitro. In the methods of the present invention, the sample or patient sample preferably may comprise any body fluid or a tissue extract. Preferred test samples include blood, serum, plasma, sputum and bronchial lavage. Preferred samples are whole blood, serum, plasma, bronchial lavage or sputum, with plasma being most preferred.

The term "assessing lung cancer" is used to indicate that the method according to the present invention will (alone or together with other markers or variables, e.g., the criteria set forth by the UICC (see above)), e.g., aid the physician to establish or confirm the absence or presence of LC or aid the physician in the prognosis, the detection of recurrence (follow-up of patients after surgery), screening and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

In a preferred embodiment the present invention relates to a method for assessing LC in vitro by biochemical markers, comprising measuring in a sample the concentration of CYBP and using the concentration determined in the assessment of LC.

The inventors of the present invention have surprisingly been able to detect the marker protein CYBP in a significant percentage of samples derived from patients with LC. Even more surprising they have been able to demonstrate that the presence and/or concentration of CYBP in such sample obtained from an individual can be used in the assessment of lung cancer.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for LC. As the skilled artisan will appreciate, no biochemical marker is diagnostic with 100% specificity and at the same time 100% sensitivity for a given multifactorial disease, for example for LC. Rather, biochemical markers, e.g., CYFRA 21-1, CEA, NSE, proGRP, SCC, or as shown here CYBP can be used to assess with a certain likelihood or predictive value, e.g., the presence, absence, or the severity of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently, e.g., using an individual cut-off for each marker, or they are combined for interpretation.

In a further preferred embodiment the assessment of LC according to the present invention is performed in a method comprising measuring in a sample the presence and/or concentration of a) CYBP, and b) one or more other marker of lung cancer, and c) using the measurement result, e.g., the concentrations determined in step (a) and step (b), respectively, in the assessment of lung cancer.

In the assessment of LC the marker CYBP will be of advantage in one or more of the following aspects: screening; diagnostic aid; prognosis; monitoring of therapy such as chemotherapy, radiotherapy, and immunotherapy.

Screening

Screening is defined as the systematic application of a test to identify individuals, e.g., at risk individuals, for indicators of a disease, e.g., the presence of lung cancer. Preferably the screening population is composed of individuals known to be at higher than average risk of lung cancer, like smokers, ex-smokers, and uranium-, quartz- or asbestos-exposed workers.

In one preferred embodiment sputum is used as a sample in the screening for lung cancer.

For many diseases, no single biochemical marker in the circulation will ever meet the sensitivity and specificity criteria required for screening purposes. This appears to be also true for lung cancer. It has to be expected that a marker panel comprising a plurality of markers will have to be used in LC screening. The data established in the present invention indicate that the marker CYBP will form an integral part of a marker panel appropriate for screening purposes. The present invention therefore relates to the use of CYBP as one marker of a LC marker panel, i.e., a marker panel comprising CYBP and one or more additional marker for LC screening purposes. Preferred additional markers are selected from the group consisting of CYFRA 21-1, CEA, NSE, proGRP and SCC.

Diagnostic Aid

Markers may either aid the differential diagnosis of benign vs. malignant disease in a particular organ, help to distinguish between different histological types of a tumor, or to establish baseline marker values before surgery.

Today, important methods used in the detection of lung cancer are radiology and/or computed tomography (CT) scans. Small nodules, i.e., small regions of suspect tissue can be visualized by these methods. However, many of these nodules—more than 90% with CT—represent benign tissues changes, and only a minority of nodules represents cancerous tissue. Use of the marker CYBP may aid in the differentiation of benign versus malign nodules.

In a preferred embodiment the marker CYBP is used in an immunohistological method in order to establish or confirm different histological types of LC.

Since CYBP as a single marker might be superior to other LC markers like CEA or NSE it has to be expected that CYBP will be used as a diagnostic aid, especially by establishing a baseline value before surgery. The present invention thus also relates to the use of CYBP for establishing a baseline value before surgery for LC.

Prognosis

Prognostic indicators can be defined as clinical, pathological, or biochemical features of cancer patients and their tumors that predict with a certain likelihood the disease outcome. Their main use is to help to rationally plan patient management, i.e., to avoid undertreatment of aggressive disease and overtreatment of indolent disease, respectively. Molina R. et al., Tumor Biol. (2003) 24:209-218 evaluated the prognostic value of CEA, CA 125, CYFRA 21-1, SSC and NSE in NSCLC. In their study abnormal serum levels of the markers NSE, CEA, and LDH (lactate dehydrogenase) appeared to indicate shorter survival.

As CYBP alone significantly contributes to the differentiation of LC patients from healthy controls, it has to be expected that it will aid in assessing the prognosis of patients suffering from LC. The level of preoperative CYBP will most likely be combined with one or more other marker for LC and/or the TNM staging system. In a preferred embodiment CYBP is used in the prognosis of patients with LC.

Monitoring of Chemotherapy

Merle, P. et al., Int. J. of Biological Markers (2004) 19:310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients. In addition, reports have described the use of CEA in monitoring the treatment of patients with LC (Fukasawa T. et al., Cancer & Chemotherapy (1986) 13:1862-1867). Most of these studies were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that CYBP will be at least as good a marker for monitoring of chemotherapy as CYFRA 21-1 or CEA, respectively. The present invention therefore also relates to the use of CYBP in the monitoring of LC patients under chemotherapy.

Follow-up

A large portion of LC patients who undergo surgical resection aimed at complete removal of cancerous tissue later develop recurrent or metastatic disease (Wagner, H., Chest (2000) 117:110-118; Buccheri, G. et al., Ann. Thorac. Surg. (2003) 75:973-980). Most of these relapses occur within the first 2-3 years after surgery. Since recurrent/metastatic disease is invariably fatal if detected too late, considerable research has focused on LC relapse at an early and thus potentially treatable stage.

Consequently, many LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G. et al., Ann. Thorac. Surg. (2003) 75:973-980). Thus, the follow-up of patients with LC after surgery is one of the most important fields of use for an appropriate biochemical marker. Due to the high sensitivity of CYBP in the LC patients investigated it is likely that CYBP alone or in combination with one or more other marker will be of great help in the follow-up of LC patients, especially in LC patients after surgery. The use of a marker panel comprising CYBP and one or more other marker of LC in the follow-up of LC patients represents a further preferred embodiment of the present invention.

The present invention in a preferred embodiment relates to the use of CYBP in the diagnostic field of LC or in the assessment of LC, respectively.

In yet a further preferred embodiment the present invention relates to the use of CYBP as a marker molecule for lung cancer in combination with one or more marker molecules for lung cancer in the assessment of lung cancer from a liquid sample obtained from an individual. Preferred selected other LC markers with which the measurement of CYBP may be combined are CYFRA 21-1, CEA, NSE, proGRP, and/or SCC. Yet further preferred the marker panel used in the assessment of LC comprises CYBP and at least one other marker molecule selected from the group consisting of CYFRA 21-1 and CEA.

As the skilled artisan will appreciate, there are many ways to use the measurements of two or more markers in order to improve the diagnostic question under investigation. In a quite simple, but nonetheless often effective approach, a positive result is assumed if a sample is positive for at least one of the markers investigated. This may, e.g., be the case when diagnosing an infectious disease, like AIDS.

Frequently, however, the combination of markers is evaluated. Preferably the values measured for markers of a marker panel, e.g., for CYBP and CYFRA 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention, e.g., to the absence or presence of LC is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I., et al, J. of Computational and Graphical Statistics, 12 (2003) 475-511; Friedman, J. H., J. of the American Statistical Association 84 (1989) 165-175; Hastie, Trevor, Tibshirani, Robert, Friedman, Jerome, The Elements of Statistical Learning, Springer Series in Statistics, 2001; Breiman, L., Friedman, J. H., Olshen, R. A., Stone, C. J. (1984) Classification and regression trees, California: Wadsworth; Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. 0., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In a preferred embodiment the present invention relates to a method for improving the diagnostic accuracy for LC versus healthy controls by measuring in a sample the concentration of at least CYBP and CYFRA 21-1, and optionally of CEA, proGRP, NSE, and/or SCC, respectively and correlating the concentrations determined to the presence or absence of LC, the improvement resulting in more patients being correctly classified as suffering from LC versus healthy controls as compared to a classification based on any single marker investigated alone.

In a preferred method according to the present invention at least the concentration of the biomarkers CYBP and CYFRA 21-1, respectively, is determined and the marker combination is used in the assessment of LC.

In a further preferred method according to the present invention at least the concentration of the biomarkers CYBP and CEA, respectively, is determined and the marker combination is used in the assessment of LC.

In a further preferred method according to the present invention at least the concentration of the biomarkers CYBP, CYFRA 21-1, and CEA, respectively, is determined and the marker combination is used in the assessment of LC.

In a further preferred method according to the present invention at least the concentration of the biomarkers CYBP, CYFRA 21-1, and proGRP, respectively, is determined and the marker combination is used in the assessment of LC.

In yet a further preferred method according to the present invention at least the concentration of the biomarkers CYBP, CYFRA 21-1, and SCC, respectively, is determined and the marker combination is used in the assessment of LC.

The following examples are provided to aid the understanding of the present invention, the true scope of which is set forth in the appended claims. It is understood that modifications can be made in the procedures set forth without departing from the spirit of the invention.

Example 1

Generation of Antibodies to the Lung Cancer Marker Protein CYBP

A polyclonal antibody preparations to the lung cancer marker protein CYBP is generated for further use of the antibody in the measurement of serum and plasma and blood levels of CYBP by immunodetection assays, e.g., Western Blotting and ELISA.

Recombinant Protein Expression in *E. coli*

In order to generate antibodies against CYBP, the recombinant antigen is produced in *E. coli*: Therefore, the CYBP coding region is PCR amplified from a full-length CYBP-cDNA clone coding for the 227 amino acids as specified in SEQ ID NO: 1 using suitable forward and reverse primers.

The forward primer features (besides the EcoRI cloning and ribosomal binding sites) oligonucleotides coding for an N-terminal MRGSHHHHHHIEGR peptide extension (SEQ ID NO: 2) introduced in-frame to the CYBP polypeptide. The EcoRI/BamHI digested PCR fragment is ligated into the corresponding pQE-30 (Qiagen, Hilden, Germany) vector fragment which is subsequently transformed into *E. coli* XL1-blue competent cells. After sequence analysis, the plasmid is transformed into *E. coli* BL21 competent cells for expression under the IPTG-inducible T5 promoter of the pQE vector series following the manufacturer's instructions.

For purification of the MRGSHHHHHHIEGR-CYBP fusion protein (fusion protein disclosed as SEQ ID NO: 3), 1 l of an over-night induced bacterial culture is pelleted by centrifugation and the cell pellet is resuspended in 20 mM sodium-phosphate buffer, 500 mM sodium chloride, pH 7.4 containing 1 mg/ml lysozyme and Complete™ EDTA-free protease inhibitor tablets. The cells are disrupted by ultrasonication and insoluble material is pelleted by centrifugation and the supernatant is applied to Ni-nitrilotriacetic acid (Ni-NTA) metal-affinity chromatography: The column is washed with several bed volumes of lysis buffer followed by washes with 20 mM sodium-phosphate buffer, 500 mM sodium chloride, 20 mM imidazol, pH 7.4. Finally, bound antigen is eluted with an imidazol gradient from 20 to 500 mM in 20 mM sodium-phosphate buffer, 500 mM sodium chloride, pH 7.4 and stored in 75 mM HEPES-buffer, pH 7.5, 100 mM sodium chloride, 1 mM EDTA, 6.5% sucrose at 4° C.

Generation of Polyclonal Antibodies a) Immunization

For immunization, a fresh emulsion of the protein solution (100 μg/ml protein CYBP) and complete Freund's adjuvant at the ratio of 1:1 is prepared. Each rabbit is immunized with 1 ml of the emulsion at days 1, 7, 14 and 30, 60 and 90. Blood is drawn and resulting anti-CYBP serum is used as described hereinbelow.

b) Purification of IgG (Immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 μl/ml of diluted sample) is added drop-wise under vigorous stirring. After 30 min the sample is centrifuged (13 000×g, 30 min, 4° C.), the pellet discarded and the supernatant collected. The pH of the supernatant is adjusted to 7.5 by the addition of 2 M Tris-base.

The immunoglobulin in the supernatant is precipitated under vigorous stirring by the drop-wise addition of a 4 M ammonium sulfate solution to a final concentration of 2 M. The precipitated immunoglobulins are collected by centrifugation (8000×g, 15 min, 4° C.).

The supernatant is discarded. The pellet is dissolved in 10 mM NaH$_2$PO$_4$/NaOH, pH 7.5, 30 mM NaCl and exhaustively dialyzed. The dialysate is centrifuged (13 000×g, 15 min, 4° C.) and filtered (0.2 μm).

c) Biotinylation of Polyclonal Rabbit IgG

Polyclonal rabbit IgG is brought to 10 mg/ml in 10 mM NaH$_2$PO$_4$/NaOH, pH 7.5, 30 mM NaCl. Per ml IgG solution 50 μl Biotin-N-hydroxysuccinimide (3.6 mg/ml in DMSO) are added. After 30 min at room temperature, the sample is chromatographed on Superdex 200 (10 mM NaH$_2$PO$_4$/NaOH, pH 7.5, 30 mM NaCl). The fractions containing biotinylated IgG are collected.

d) Digoxigenin Conjugation of Polyclonal Rabbit IgG

Polyclonal rabbit IgG is brought to 10 mg/ml in 10 mM NaH$_2$PO$_4$/NaOH, 30 mM NaCl, pH 7.5. Per ml IgG solution 50 μl digoxigenin-3-O-methylcarbonyl-E-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on Superdex® 200 (10 mM NaH$_2$PO$_4$/NaOH, pH 7.5, 30 mM NaCl). The fractions containing digoxigenylated IgG are collected.

Example 2

ELISA for the Measurement of CYBP in Human Serum and Plasma Samples

For detection of CYBP in human serum or plasma, a sandwich ELISA is developed. For capture of the antigen, anti-CYBP polyclonal antibody (see Example 1) is conjugated with biotin and immobilized on a streptavidin-coated surface and for detection of the antigen anti-CYBP polyclonal antibody is conjugated with digoxigenin.

Streptavidin-coated microtiter plates are incubated with 100 μl biotinylated anti-CYBP polyclonal antibody (1 μg/ml) per well for 10 min at room temperature. Subsequently plates are washed three times with PBS, 0.05% Tween 20. Wells are then incubated for 2 h with either a serial dilution of the recombinant protein (see Example 1) as standard antigen or with diluted EDTA-plasma samples from patients together with 5 μg/ml digoxigenin-conjugated anti-CYBP polyclonal antibody. Incubation was in an incubation buffer (PBS comprising 0.1% Tween 20, 1% BSA). Thereafter, plates are washed three times to remove unbound components. In a next step, wells are incubated with 20 mU/ml anti-biotin-digoxigenin-peroxidase conjugate for 60 min. Plates are subsequently washed three times with the same buffer. For detection of bound antigen-antibody complexes, wells are incubated with 200 μl TMB (tetramethyl benzidine) solution (Roche Diagnostics GmbH, Mannheim, Germany, Catalog No. 120 344 25 001) for 15 min, stopped by addition 50 μl of 1N sulfuric acid and OD is measured at 450 nm (with 620 nm as a reference wave length) with an ELISA reader.

Example 3

Study Population

Samples derived from 60 well-characterized NSCLC patients (30 adeno-CA, 30 squamous cell CA) are used.

The levels of CYBP, CEA and CYFRA21-1 in the LC samples are evaluated.

The results are shown in Table 1.

TABLE 1

|  | CEA [ng/ml] | CYFRA 21-1 [ng/ml] | CYBP (EDTA) [μg/ml] |
| --- | --- | --- | --- |
| Cut-off (95% Blood donors): | >5.5 | >2.1 | >9.29 |
| number of samples | 60 | 60 | 60 |
| number positive | 19 | 43 | 49 |
| Sensitivity (%): | 32 | 72 | 82 |
| number of samples Adeno | 30 | 30 | 30 |
| number positive Adeno | 13 | 19 | 25 |
| Sensitivity (%) Adeno: | 43 | 63 | 83 |
| number of samples squamous | 30 | 30 | 30 |
| number positive squamous | 6 | 24 | 24 |
| Sensitivity (%) squamous | 20 | 80 | 80 |
| Cut-off (90% Blood donors): | >3.9 | >1.6 | >8.58 |
| number of samples | 60 | 60 | 60 |
| number positive | 24 | 47 | 50 |
| Sensitivity (%): | 40 | 78 | 83 |

With a cut-off value of 9.29 μg/ml the sensitivity of CYBP in all LC samples is 82%, for adenocarcinoma samples 83% and for squamous cell carcinoma samples 80% respectively. This sensitivity was surprising and is significantly higher than the sensitivity of CEA and CYFRA 21-1.

What is claimed is:

1. A method for in vitro diagnosis of lung cancer in a patient, the method comprising:
   contacting a serum or plasma sample from the patient with an antibody having specific binding affinity for calcyclin-binding protein (CYBP) set forth as SEQ ID NO:1,
   measuring an amount of CYBP in the sample based on the contacting step,
   comparing the measured amount of CYBP with a cut-off value for CYBP, and,
   diagnosing lung cancer if the measured amount of CYBP is greater than a cut-off value for CYBP.

2. The method according to claim 1, further comprising contacting a sample from the patient with an antibody having specific binding affinity for an additional marker selected from the group consisting of soluble 30 kDa fragment of cytokeratin 19 (CYFRA 21-1), carcinoembryonic antigen (CEA), neuron-specific enolase (NSE), pro-gastrin-releasing peptide (proGRP) and squamous cell carcinoma antigen (SCC), measuring an amount of the additional marker based on the contacting step, comparing the measured amount of additional marker with a cut-off value for additional marker, and diagnosing lung cancer if the measured amounts of CYPB and additional marker are greater than the cut-off values for CYPB and additional marker.

3. The method according to claim 2, wherein the additional marker is CYFRA 21-1.

4. The method according to claim 2, wherein the additional marker is CEA.

5. The method according to claim 2, wherein the additional marker is SCC.

6. The method according to claim 1, wherein the patient belongs to a population of individuals having a greater than average risk of lung cancer.

7. The method according to claim 1, wherein the cut-off value for CYBP is derived from a population having a particular histological type of lung cancer tumor and diagnosing comprises differentially diagnosing histological type of lung cancer tumor based on the comparison step.

8. The method according to claim 1, wherein the cut-off value for CYBP is derived from a patient prior to treatment of the patient for lung cancer.

9. The method according to claim 1, wherein the antibody has a binding affinity of at least $10^7$ l/mol.

10. The method according to claim 1, wherein the antibody binds to a biomolecule other than CYBP with a binding affinity which is at most 10% or less of the binding affinity to CYBP.

11. The method according to claim 1, wherein having a specific binding affinity is defined as having a binding affinity to CYBP of at least $10^7$ l/mol while having a binding to a biomolecule other than CYBP which is at most 10% or less of the binding affinity to CYBP.

12. The method according to claim 1, wherein the cut-off value is determined from a group of healthy individuals.

13. The method according to claim 1, wherein the cut-off value is set to result in a specificity of 90%.

14. The method according to claim 1, wherein the cut-off value is set to result in a specificity of 95%.

\* \* \* \* \*

SEQUENCE LISTING

<160> NUMBER OF SEQ ID NOS: 3

<210> SEQ ID NO 1
<211> LENGTH: 227
<212> TYPE: PRT
<213> ORGANISM: Homo sapiens

<400> SEQUENCE: 1

Ala Ser Glu Glu Leu Gln Lys Asp Leu Glu Glu Val Lys Val Leu Leu
1               5                   10                  15

Glu Lys Ala Thr Arg Lys Arg Val Arg Asp Ala Leu Thr Ala Glu Lys
            20                  25                  30

Ser Lys Ile Glu Thr Glu Ile Lys Asn Lys Met Gln Gln Lys Ser Gln
        35                  40                  45

Lys Lys Ala Glu Leu Leu Asp Asn Glu Lys Pro Ala Ala Val Val Ala
    50                  55                  60

Pro Ile Thr Thr Gly Tyr Thr Val Lys Ile Ser Asn Tyr Gly Trp Asp
65                  70                  75                  80

Gln Ser Asp Lys Phe Val Lys Ile Tyr Ile Thr Leu Thr Gly Val His
                85                  90                  95

Gln Val Pro Thr Glu Asn Val Gln Val His Phe Thr Glu Arg Ser Phe
            100                 105                 110

Asp Leu Leu Val Lys Asn Leu Asn Gly Lys Ser Tyr Ser Met Ile Val
        115                 120                 125

Asn Asn Leu Leu Lys Pro Ile Ser Val Glu Gly Ser Ser Lys Lys Val
    130                 135                 140

Lys Thr Asp Thr Val Leu Ile Leu Cys Arg Lys Lys Val Glu Asn Thr
145                 150                 155                 160

Arg Trp Asp Tyr Leu Thr Gln Val Glu Lys Glu Cys Lys Glu Lys Glu
                165                 170                 175

Lys Pro Ser Tyr Asp Thr Glu Thr Asp Pro Ser Glu Gly Leu Met Asn
            180                 185                 190

Val Leu Lys Lys Ile Tyr Glu Asp Gly Asp Asp Asp Met Lys Arg Thr
        195                 200                 205

Ile Asn Lys Ala Trp Val Glu Ser Arg Glu Lys Gln Ala Lys Gly Asp
    210                 215                 220

Thr Glu Phe
225

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide extension

<400> SEQUENCE: 2

Met Arg Gly Ser His His His His His His Ile Glu Gly Arg
1               5                   10

<210> SEQ ID NO 3
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Arg Gly Ser His His His His His Ile Glu Gly Arg Ala Ser
1               5                   10                  15

Glu Glu Leu Gln Lys Asp Leu Glu Val Lys Val Leu Leu Glu Lys
            20                  25              30

Ala Thr Arg Lys Arg Val Arg Asp Ala Leu Thr Ala Glu Lys Ser Lys
        35                  40                  45

Ile Glu Thr Glu Ile Lys Asn Lys Met Gln Gln Lys Ser Gln Lys Lys
    50                  55                  60

Ala Glu Leu Leu Asp Asn Glu Lys Pro Ala Ala Val Val Ala Pro Ile
65              70                  75                      80

Thr Thr Gly Tyr Thr Val Lys Ile Ser Asn Tyr Gly Trp Asp Gln Ser
            85                  90                  95

Asp Lys Phe Val Lys Ile Tyr Ile Thr Leu Thr Gly Val His Gln Val
            100             105             110

Pro Thr Glu Asn Val Gln Val His Phe Thr Glu Arg Ser Phe Asp Leu
        115             120             125

Leu Val Lys Asn Leu Asn Gly Lys Ser Tyr Ser Met Ile Val Asn Asn
        130             135             140

Leu Leu Lys Pro Ile Ser Val Glu Gly Ser Ser Lys Lys Val Lys Thr
145             150             155             160

Asp Thr Val Leu Ile Leu Cys Arg Lys Lys Val Glu Asn Thr Arg Trp
                165             170             175

Asp Tyr Leu Thr Gln Val Glu Lys Glu Cys Lys Glu Lys Glu Lys Pro
            180             185             190

Ser Tyr Asp Thr Glu Thr Asp Pro Ser Glu Gly Leu Met Asn Val Leu
        195             200             205

Lys Lys Ile Tyr Glu Asp Gly Asp Asp Met Lys Arg Thr Ile Asn
    210             215             220

Lys Ala Trp Val Glu Ser Arg Glu Lys Gln Ala Lys Gly Asp Thr Glu
225             230             235             240

Phe
```